(12) United States Patent
Caruso et al.

(10) Patent No.: US 6,833,192 B1
(45) Date of Patent: Dec. 21, 2004

(54) ENCAPSULATION OF CRYSTALS VIA MULTILAYER COATINGS

(75) Inventors: Frank Caruso, Golm (DE); Dieter Trau, Kowloon (HK); Helmuth Möhwald, Bingen (DE); Reinhard Renneberg, Kowloon (HK)

(73) Assignee: Max-Planck Gesellschaft Zur Forderrung der Wissenschaften E.V., Munich (DE)

( * ) Notice: Subject to any disclaimer, the term of this patent is extended or adjusted under 35 U.S.C. 154(b) by 74 days.

(21) Appl. No.: 10/018,325

(22) PCT Filed: Jun. 9, 2000

(86) PCT No.: PCT/EP00/05358

§ 371 (c)(1),
(2), (4) Date: Mar. 25, 2002

(87) PCT Pub. No.: WO00/77281

PCT Pub. Date: Dec. 21, 2000

(30) Foreign Application Priority Data

Jun. 10, 1999 (EP) ............................... 99111334

(51) Int. Cl.⁷ ................................................ B32B 5/16
(52) U.S. Cl. ........................ 428/403; 427/2.1; 427/128; 427/189; 427/190; 427/212; 428/900
(58) Field of Search .................. 427/2.1, 128, 189, 427/190, 212; 428/403, 900

(56) References Cited

U.S. PATENT DOCUMENTS

| | | | |
|---|---|---|---|
| 4,001,140 A | | 1/1977 | Foris et al. |
| 5,091,187 A | | 2/1992 | Haynes |
| 5,344,487 A | * | 9/1994 | Whalen-Shaw ............. 106/416 |
| 5,427,767 A | * | 6/1995 | Kresse et al. ............... 424/9.32 |
| 5,512,332 A | * | 4/1996 | Liberti et al. ............... 427/550 |
| 5,705,222 A | | 1/1998 | Somasundaran et al. |
| 5,716,709 A | | 2/1998 | Ferguson et al. |
| 6,203,909 B1 | * | 3/2001 | Chassot ...................... 428/403 |
| 6,423,338 B1 | * | 7/2002 | Larson et al. ............... 424/450 |
| 6,479,146 B1 | * | 11/2002 | Caruso et al. ............. 428/403 |
| 6,689,478 B2 | * | 2/2004 | Laguitton ................... 428/441 |

FOREIGN PATENT DOCUMENTS

| | | | |
|---|---|---|---|
| EP | 0 336 014 | 10/1989 | |
| EP | 0 516 252 | 12/1992 | |
| EP | 540582 B1 | * 8/1994 | .......... A61K/31/36 |
| WO | 92 00998 | 1/1992 | |

OTHER PUBLICATIONS

Decher G. et al., "Building of Ultrathin Multilayer Films by a Self–Assembly Process: III. \Consecutively Alternating Adsorption of Anionic and Cationic Polyelectrolytes on Charged Surfaces", 1992 Thin Solid Films, vol. 210–211, No. 1–2, Part 2, pp. 831–835.

Meldrum F.C. et al., "Magnetoferritin: In Vitro Synthesis of a Novel Magnetic Protein", 1992 Science, vol. 257, pp. 522–523.

Caruso et al., "Investigations of electrostatic interactions in polyelectrolyte multilayer films . . . ", 1999 Macromolecules, vol. 32, pp. 2317–2328.

Kawahashi, N. et al, "Preparation and Properties of Uniform Coated Colloidal Particles Yttrium Basic Carbonate on Polystyrene Latex", 1990 Journal of Colloid and Interface Science, vol. 138, pp. 534–542.

Philipse, "Magnetic silica dispersions . . . ", 1994 Langmuir, vol. 10, pp. 92–99.

* cited by examiner

Primary Examiner—H. Thi Le
(74) Attorney, Agent, or Firm—Sutherland Asbill & Brennan LLP (57) ABSTRACT

The invention refers to a new process for preparing coated crystals by coating crystal template particles with alternating layers of oppositely charged polyelectrolytes and/or nanoparticles.

34 Claims, 5 Drawing Sheets

ENCAPSULATION OF CRYSTALS VIA MULTILAYER COATINGS

The invention refers to a new process for preparing coated crystals by coating crystal template particles with alternating layers of oppositely charged polyelectrolytes and/or nanoparticles.

The area of thin film fabrication, in which ordered, functional supramolecular structures are the chief goal, has been greatly impacted by the recent introduction of the layer-by-layer (LbL) self-assembly technique (Decher, Science 1997, 277, 1232). The LbL method permits the fabrication of multilayer thin film assemblies on solid supports by the spontaneous sequential adsorption of oppositely charged species from dilute aqueous solutions onto charged substrates. The driving force for the multilayer film build-up is primarily due to the electrostatic attraction and complex formation between the charged species deposited. The LbL approach was initially employed to construct multilayer films of polyelectrolytes (Decher, Science 1997, 277, 1232), and subsequently extended to include proteins (Lvov et al, J. Am. Chem. Soc. 1995, 117, 6117; Onda et at, T. Biotech. Bioeng. 1996, 51, 163; Caruso et al, Langmuir 1997, 13, 3427), nucleic acids (Decher et al, J. Biosens. Bioelectron. 1994, 9, 677; Sukhorukov et al, Thin Solid Films 1996, 284/285, 220; Caruso et al, Anal. Chem. 1997, 69, 2043), dyes (Araki et al, Langmuir 1996, 12, 5393; Yoo et al, Synthetic Metals 1997, 85, 1425; Ariga et al, J. Am. Chem. Soc. 1997, 119, 2224), dendrimers (Tsukruk et al, Langmuir 1997, 13, 2171), and various inorganic nanoparticles (Kleinfeld et al, Science 1994, 265, 370; Keller et al, J. Am. Chem. Soc. 1994, 116, 8817; Kotov et al, J. Am. Chem. Soc. 1997, 119, 6821; Kotov et al, J. Phys. Chem. 1995, 99, 13065; Feldheim et al, J. Am. Chem. Soc. 1996, 118, 7640; Schmitt et al, Adv. Mater 1997, 9, 61; Lvov et al, Langmuir 1997, 13, 6195) in polyelectrolyte multilayer assemblies by replacing one of the polyions by a similarly charged species.

The vast majority of studies concerning the LbL technique have employed macroscopically flat charged surfaces as substrates for multilayer film formation. For example, U.S. Pat. No. 5,716,709 describes multilayered nanostructures comprising alternating organic and inorganic ionic layers on a flat substrate, such as a silicon wafer. Recently, Keller et al reported the preparation of alternating composite multilayers of exfoliated zirconium phosphate sheets and charged redox polymers on (3-aminopropyl)-triethoxysilane-modified silica particles (Keller et al, J. Am. Chem. Soc. 1995, 117, 12879).

In more recent studies (Caruso et al., Macromolecules, 1999, 32, 2317; Caruso et al., J. Phys. Chem. B. 1998, 102, 2011; Sukhorukov et al., Colloids Surf. A: Physicochem.Eng.Aspects 1998, 137, 253), the LbL approach was successfully applied to utilise submicron- and micron-sized charged colloidal particles as the adsorbing substrates to produce colloid-supported polyelectrolyte multilayer films: regular step-wise polyelectrolyte multilayer growth was observed on the colloids.

Considerable scientific effort has focussed on the fabrication of composite micro- and nanoparticles that consist of either organic or inorganic cores coated with shells of different chemical composition (Kawahashi and Matijevic, J.Colloid Interface Sci. 1991, 143, 103; Garg and Matijevic, J.Colloid Interface Sci. 1988, 126; Kawahashi and Matijevic, J.Colloid Interface Sci. 1990, 138, 534; Ohmori and Matijevic, J.Colloid Interface Sci. 1992, 150, 594; Giersig et al., Adv. Mater. 1997, 9, 570; Liz-Marzan et al., Langmuir 1996, 12, 4329; Liz-Marzan et al., J.Chem.Soc. Chem.Commun. 1996, 731; Giersig et al., Ber.Bunsenges. Phys.Chem. 1997, 101, 1617; Correa-Duarte et al., Chem.Phys.Lett. 1998, 286, 497; Bamnolker et al., J.Mater.Sci.Lett. 1997, 16, 1412; Margel and Weisel, J.Polym. Sci.Chem.Ed. 1984, 22, 145; Philipse et al., Langmuir 1994, 10, 92). These core-shell particles often exhibit properties which are significantly different to those of the templated core (e.g. different surface chemical composition, increased stability, higher surface area, as well as different magnetic and optical properties), thus making them attractive both from a scientific and technological viewpoint. Applications for such particles are diverse, ranging from capsule agents for drug delivery, catalysis, coatings, composite materials, as well as for protecting senstitive agents such as enzymes and proteins. Previous investigations have demonstrated that polymeric microparticles and inorganic cores can be coated with uniform layers of various materials, including silica, yttrium basic carbonate, zirconium hydrous oxide, either by controlled surface precipitation reactions on the core particles, or by direct surface reactions.

U.S. Pat. No. 5,091,187 discloses the coating of microcrystals with phospholipids. EP-A-0 516 252 discloses the coating of nanocrystalline-magnetic particles with natural or synthetic glycosamino-glucans which may be selected from chondroitin-sulphate, dermatan-sulphate, heparan-sulphate, heparin and analogs thereof.

U.S. Pat. No. 5,705,222 discloses a process for preparing composite particle dispersions wherein a plurality of core particles is dispersed in a first solution wherein the core particles do not irreversibly self-flocculate, an amount of polymer is added to the dispersion of core particles, wherein the polymer has an affinity for the dispersed core particles and the excess polymer is removed by a solid/liquid separation process, i.e. centrifugation or decanting.

In DE 198 12 083.4 it was suggested that soluble colloidal cores can be used as templates for the sequential deposition of polyelectrolytes to fabricate novel three-dimensional hollow polymer shells. From PCT/EP99/01854 the preparation of coated capsules and hollow shells by coating colloidal particles with alternating layers of oppositely charged nanoparticles and polyelectrolytes is known. DE 199 075 52.2 discloses a process for preparing capsules having a polyelectrolyte shell wherein the template particles are selected from aggregates of biological and/or amphiphilic materials such as cells, cell aggregates, subcellular particles, virus particles and aggregates of biomolecules.

The coating of biocrystals, however, represents several challenges which are not applicable when templating other solid core particles including biological templates. First, the crystals are formed under delicate solution conditions, hence suitable conditions have to be found which facilitate polymer multilayer deposition on the crystal surface and do not destroy the crystal morphology (i. e. to avoid its solubilization), and second, the permeability of the polymer capsule walls must be such that it permits encapsulation of the bio-crystal. In addition, since the primary usefulness of biological molecules is their biological function, their activity should be preserved when encapsulated.

Herein we report sucessful coating of crystals, e. g. bio-crystals by depositing alternating layers of oppositely charged polyelectrolytes and/or nanoparticles on crystal template particles via the sequential electrostatic adsorption of polyelectrolyte and/or nanoparticles from solution. Functional biomolecules are obtainable after solubilization within the polyelectrolyte/nanoparticle shell and/or after removal of the shell.

Thus, a first aspect of the present invention is a process for preparing coated crystals comprising the steps:

(a) providing a dispersion of crystal template particles in a solvent and (b) coating said particles with a multilayer comprising alternating layers of oppositely charged polyelectrolytes and/or nanoparticles. Suitable crystal template particles are particles of crystallized substances. Preferably the crystals are particles of crystallized organic compounds and/or particles of crystallized biomolecules (bio-crystals) (including molecules which occur in living organisms and/or which influence the metabolism of living organisms). E. g. the crystals may be selected from crystals of proteins, peptides, nucleic acids, lipids, carbohydrates, saccharides, drugs etc., whereas protein crystals are preferred. Examples of protein crystals are crystals of antibodies, enzymes, such as oxidoreductases, transferases, hydrolases, lyases, isomerases and ligases, virus capsid protein crystals, peptide crystals, S-layer protein crystals, glycoprotein crystals, receptor protein crystals and cytosolic protein crystals. The proteins may be natural, recombinant and/or synthetic proteins. Examples of nucleic acid crystals are crystalline DNA, crystalline RNA and crystalline oligonucleotides. Examples of crystalline low molecular weight materials are crystalline drugs, crystalline vitamins, crystalline nutrients, crystalline hormones and crystalline organic or inorganic salts.

It is also possible to use crystal template particles from crystalline bio-material, crystalline organic material, crystalline inorganic material or mixtures thereof. Examples of crystalline organic material are crystalline drugs, vitamins, nutrients, hormones, growth factors, pesticides and antibiotics.

The crystalline template particles may be derived from a single crystal or an amorphous crystal material. Suitable crystal template particles may be obtained, for example, from natural sources, may be prepared recombinantly, synthetically or by a cell culture or may be a PCR product.

Preferably, the template particles have an average diameter of up to 500 µm, in particular, $\leq 50$ µm, more particularly $\leq 10$ µm, more preferably $\leq 5$ µm, and most preferably $\leq 2$ µm. The minimum diameter of the template particles is preferably 10 nm, more preferably 100 nm, most preferably 200 nm and, in particular, 1 µm. The structure or shape of the template may be in any desired form, e. g. rectangular, square, spherical, triangular and various other forms depending on the structure of the crystal to be templated.

Important advantages of the crystal templating procedure presented are its versatility and generality. The thickness of the polymer walls can be controlled by varying the number of polyelectrolyte/nanoparticle deposition cycles, thus providing a straightforward and simple means to vary the permeability of the capsules. It can also be used to encapsulate biological materials in crystalline form in order to perform chemical reactions, e.g. enzymatic reactions. Furthermore, the entire volume of the capsule consists of an active biomolecule, making the activity per volume of the encapsulated biomolecule several orders of magnitude higher than that of conventional or immobilized biomolecules. This has the advantage of reducing the reaction times and the volume of biomolecule required, and maximizes activity and productivity. The multilayer coating also provides a way to preserve and/or prolong the activity of the encapsulated biomolecules by protecting them in environments where certain substances, e. g. macromolecules, degrading enzymes, e.g. proteases, nucleases, etc., microorganisms, inhibitors etc. may cause their degradation.

The successful encapsulation of bio-crystals by the nanoscale engineering of polymer capsules on bio-crystal templates as demonstrated here, coupled with the easy diffusion of small mobile substrates and reaction products through the polymer walls, is a promising way to both control and increase the efficiency of catalytic processes. Combining these templating process with recently developed techniques that allow the layering of various enzyme layers on colloids yields enzyme nanoreactor systems for sequential biocatalytic reactions. Columns packed with the biocrystal loaded capsules can be used for chromatographic separations and—in the case of encapsulated enzymes—as catalytic converters. Further, the introduction of functionalities, e. g. magnetic properties, by incorporation of suitable nanoparticles in the polymer walls provides a multifunctional system with a plurality of properties. Together, these developments provide outstanding opportunities to produce tailored and optimized systems for numerous applications in the biotechnology area.

The process according to the present invention comprises coating the template particles with coatings of polyelectrolyte molecules and/or nanoparticles. The polyelectrolytes are usually polymers having ionically dissociable groups which may be a component or substituent of the polymer chain. Preferably, linear or/and water-soluble polyelectrolytes are used. However, polyelectrolytes being non-linear polymers or mixtures of linear and non-linear polymers also can be used. Depending on the type of dissociable group, polyelectrolytes are subdivided into polyacids and polybases. Upon dissociation polyacids separate protons to give polyanions. Examples of polyacids are polyphosphoric acid, polyvinyl or polystyrene sulphuric acid, polyvinyl or polystyrene sulfonic acid, polyvinyl or polystyrene phosphonic acid and polyacrylic acid. Examples of the respective salts, which are also called polysalts, are polyphosphate, polysulphate, polysulfonate, polyphosphonate and polyacrylate.

Polybases contain groups which are capable of accepting protons, e.g. by reacting with acids to give salts. Examples of polybases are polyamines, such as polyethylene amine, polyvinyl amine and polyvinyl pyridine or poly(ammonium salts), such as poly (diallyl dimethylammonium chloride). Polybases form polycations by accepting protons.

The polyelectrolytes may be or may be based on organic polymers, inorganic polymers and biopolymers or mixtures thereof. Preferred examples of organic polymers are biodegradable polymers such as polyglycolic acid (PGA), polylactic acid (PLA), polyamides, poly-2-hydroxy butyrate (PHB), polycaprolactone (PCL), poly(lactic-co-glycolic) acid (PLGA) and copolymers thereof. Further preferred examples of polyelectrolytes are labelled polymers, e, g. fluorescently labelled polymers, conducting polymers, liquid crystal polymers, photoconducting polymers and photochromic polymers as well as copolymers thereof. Still further preferred examples of polyelectrolytes are sillafines, i.e. silicon containing cationic polyelectrolytes (cf. Science 286 (1999), 1129–1132).

Preferred examples of suitable biopolymers are poly amino acids such as peptides or S-layer proteins, poly carbohydrates such as dextrins, pectins, alginates, glycogens, amyloses or chitins, polynucleotides, e. g. DNA, RNA, oligonucleotides, gelatins (gelatin A, gelatin B) or modified biopolymers, e. g. carboxymethyl cellulose, carboxymethyl dextran or lignin sulfonates.

Preferred examples of suitable inorganic polymers, based on which the polyelectrolytes can be created, are polysilanes and silanoles, polyphosphazenes, polysulfazenes and polysulfides and polyphosphates.

The polyelectrolytes can be cross-linked after templating. The cross-linking can be done between the polymers in one layer or/and between polymers of different layers.

The nanoparticles preferably have an average diameter from 1 to 100 nm, more preferably from 5 to 50 nm and most preferably from 10 to 20 nm. The structure or shape of the nanoparticle may be in any desired form, with the most preferable shape being spherical and/or monodisperse.

The nanoparticles may be selected from inorganic, organic and biological materials. Preferred examples of inorganic particles are ceramic particles, e.g. oxidic ceramic particles, such as silicon dioxide, titanium dioxide, zirconium dioxide optionally doped with other metal oxides, magnetic particles such as iron oxide-containing particles such as $Fe_3O_4$, magneto-optical particles, nitridic ceramic particles, e.g. $Si_3N_4$, carbidic ceramic particles, metallic particles, e.g. gold, silver, palladium and sulfur or selene-containing particles such as cadmium sulfide, cadmium selenide etc. Especially preferred are particles having magnetic properties. Examples of organic or biological nanoparticles are macromolecules, such as polypeptides, proteins, nucleic acids, enzymes, antibodies, receptor/ligand systems etc. and targeting molecules for therapeutical applications. Especially preferred biological nanoparticles are proteins, e.g. immunologically reactive proteins such as antigens and antibodies, e.g. IgG, or targeting molecules for therapeutical applications. Further, the biological nanoparticles may be deposited as conjugates containing a labelling group, e.g. a fluorescent group such as fluorescein. The resulting particles are suitable for analytical, e.g. immunological, detection methods. Further, an immobilization of enzymes, single enzymes or a plurality of enzymes, e.g. members of an enzymatic cascade, in single layers or different layers is of special interest because of the ability to increase the catalysis efficiency. Substrates could readily diffuse through the film and react with the immobilized enzyme, thereby producing product.

For the preparation of the coated particles according to the present application a dispersion of crystal template particles in suitable solvent is provided. A suitable solvent is a solvent where the crystal may be encapsulated. In some cases the solvent is an aqueous solvent. In other cases the solvent may be a mixture of an aqueous solvent with organic solvents. Still in other cases the solvent may be a pure organic solvent. Among the organic solvents polar solvents are preferred, e. g. polar protic solvents such as alcohols or polar aprotic solvents such as esters. Preferred examples of aqueous solvents are aqueous buffers which optionally contain detergents and/or antifoaming and/or antimicrobial agents. Aqueous solvents preferably contain buffer salts for pH and/or ionic strength adjustment. Preferred examples of mixed solvents are mixtures of water or aqueous buffers with polar protic organic solvents such as alcohols, organic acids, amines, pyridin or mercaptanes or mixtures of water or buffer with polar aprotic organic solvents such as ketones, esters, ethers, ethyleneglycols, nitrites, formamide, alkylated formamides, nitroalkanes and dialkylsulfoxides. Preferred examples of organic solvents are polar protic organic solvents such as alcohols, organic acids, amines, pyridines, mercaptanes or mixtures thereof and polar aprotic organic solvents such as ketones, esters, ethers, ethyleneglycols, nitrites, formamide, alkylated formamides, nitroalkanes, dialkylsulfoxides and mixtures thereof. Of course also mixtures of protic and aprotic solvents may be used.

The dispersion of the template particles in the solvent may contain a salt, e.g. NaCl or KAc in a concentration which preferably ranges from 50 mmole/l to 1 mole/l. The solvent, pH, the temperature and the salt concentration in the dispersion are adjusted that the respective crystal template particles which are to be encapsulated are not substantially dissolved. Encapsulation temperatures of from 0° C. to 10° C., e. g. 4° C. are preferred. E. g., the encapsulation of catalase enzyme crystals may be carried out in an aqueous solution of 1 M potassium acetate, pH 5, 4° C. Alternating layers of oppositely charged components, i.e. polyelectrolyte molecules and/or nanoparticles, different types of nanoparticles or combinations thereof are then deposited on said template particles. The pH of the dispersion is adjusted in such a way that the molecules, e.g. polyelectrolyte molecules and nanoparticles, each have opposite total charges, thus facilitating their deposition via electrostatics. The thickness of the coating which is determined by the number of layers is preferably 2 to 1000 nm, with 2 to 40 and particularly 2 to 20, e.g. 3 to 10 coatings being applied. Suitably, each layer may be comprised of a single species of polyelectrolyte and/or nanoparticle or of a mixture comprising at least two polyelectrolyte and/or nanoparticle species. Further, for each layer different polyelectrolyte and/or nanoparticle species may be used.

After application of each layer the excessive molecules (e.g. polyelectrolyte and/or nanoparticle) which have not contributed to forming the layer are preferably separated off before the next layer is applied. Such separation can be done according to any known method, particularly centrifugation, filtration and/or dialysis.

In a preferred embodiment of the invention the template particles are at first coated with several layers of oppositely charged cationic and anionic polyelectrolytes before the alternating layers of nanoparticles and polyelectrolyte or the alternating nanoparticle layers are applied. The coating of template particles with several layers of oppositely charged polyelectrolytes is described in DE 198 12 083.4 to which express reference is made. Preferably, the template particles are coated with at least two and up to six layers of oppositely charged cationic and anionic polyelectrolytes, e.g. with three layers. The outermost polyelectrolyte layer is preferably oppositely charged with regard to the polyelectrolyte/nanoparticle to be deposited.

The thickness of the shell walls around the template particles can be readily controlled by varying the number of deposition cycles, whilst the shell size and shape are predetermined by the dimensions of the template particle employed. The thickness of the shell can vary in a wide range, e.g. from 2 to 1000 nm, particularly from 5 to 250 nm. The capsule thickness and permeability for controlled release of encapsulated material can be controlled by the number of layers, by the nature of the polyelectrolytes and/or nanoparticles used and, if desired, by an additional cross-linking step.

Excessive molecules, e.g. polyelectrolytes and/or nanoparticles which do not contribute to forming the layers may be separated after each templating step. The separation can be done, e.g. by centrifugation, filtration, dialysis or by sorting technologies regarding a special property, such as optical or magnetic properties. By the process of the invention the template crystals may be obtained encapsulated after the templating process.

It is possible to at least partially solubilize the encapsulated crystals after the coating has been completed. The solubilization can be carried out by adjustment of solvent, pH, temperature and/or salt conditions. The solubilized compounds, e. g. biomolecules substantially retain their functionality, e. g. biological activity after encapsulation and subsequent solubilization.

Further, it was found that the capsule walls can be ruptured or dissolved under conditions which do not significantly impair the activity of the encapsulated biomolecules (as crystals or after solubilization). The capsule walls may be dissolved by adjusting appropriate conditions, such as pH, e. g. under alkaline or acidic conditions, by means of chemical or biochemical degradation, or by physical methods, e. g. ultrasound.

Of particular importance for the use of the coated particles is the permeability of the shell wall. The permeability of the shell wall can be influenced by the selection of the polyelectrolytes used for the shell, the wall thickness and the ambient conditions. It is thus possible to selectively determine and change the permeability properties. Further, the permeability of the shell wall can be influenced by partially dissolving parts of the shell walls, e. g. by using a deproteinizer.

The permeability properties can be further modified by pores in at least one of the layers. Such pores can be formed by the polyelectrolytes or nanoparticles themselves if suitably chosen. By incorporating selective transport systems such as carriers or channels into the polyelectrolyte shell the transversal transport properties of the shell can be adapted to the respective application. The pores or channels of the shell wall can be selectively opened and closed, respectively, by chemically modifying and/or changing the ambient conditions. A high salt concentration of the medium used for the deposition of the polyelectrolyte results in a low packing density and a high permeability of the shell wall. On the other hand, a high salt concentration of the medium used for the deposition of the nanoparticles results in a high packing density. Thus, by adjusting the salt concentrations in the deposition medium, the permeability of the shell can be controlled, as desired. Further, the permeability properties of the shell may be modified by selecting the conditions for decomposing the core, e.g. by selecting the temperature and heating conditions in a calcination procedure.

Still another method to modify the permeability of the shell walls is the deposition of one or several lipid layers on the outside of the shell wall or as an intermediate layer. Furthermore, the permeability may be modified by deposition of S-layer proteins. These proteins are able to build monolayers having a thickness of e. g. 5–20 nm by self-assembling on surfaces. These monolayers have a very defined structure and also a defined pore size of e. g. 4–8 nm. Incorporating such proteins in the capsule wall allows a further control of the capsule permeability properties.

Finally, the templated biomolecules can be at least partially disintegrated after the coating has been completed. They can be disintegrated in appropriate reagents, e. g. deproteinizer solutions or thermally (e.g. by calcination to temperatures of at least 500° C.). After dissolution of the biomolecules hollow shells remain which are composed of polyeletrolyte material, nanoparticle material or optionally polyelectrolyte and nanoparticle material. The resulting hollow shells may be inorganic or organic shells or composite inorganic-organic or composite inorganic-inorganic shells depending on the method of core removal. For example, when thermal treatment (calcination) is used, all organic matter is removed, hence only inorganic shells are obtained. Exposure to deproteinizer solutions to remove the core results in polyelectrolyte shells or composite hollow particles in which the core is removed but the polyelectrolyte assembled between the nanoparticle layers remains in the shell.

The hollow shells may be characterized by any known methods, e.g. by scanning and transmission electron microscopy and atomic force microscopy. Preferably, the shells are uniform layers of regular thickness and can find applications in numerous areas, such as medicine, pharmaceutics, catalysis, optics, magnetics, separation and sensing. In the hollow shells of the present invention active agents, e.g. inorganic or/and organic substances can be encapsulated. Examples of active agents are pharmaceutic agents so that the shells can be used as drug delivery systems in order to transport the active agents to the desired place in the organism. Further, also contrasting agents can be enclosed in the shells, e.g. to improve the quality of images obtained by ultrasonic examination. It is also possible that the hollow shells themselves are used as contrasting agents.

A further aspect of the present invention is a coated crystal particle, preferably a bio-crystal particle having a core which is a template particle and a multilayer shell comprising alternating layers of oppositely charged inorganic polyelectrolytes and/or nanoparticles. Still a further aspect of the present invention is a coated particle having a core comprising an at least partially solubilized crystal template particle, preferably a bio-crystal particle and a multilayer shell comprising alternating layers of oppositely charged polyeletrolytes and/or nanoparticles. Preferably, the average diameter of the coated particle is 15 $\mu$m or less, more preferably 100 nm to 10 $\mu$m.

Still a further aspect of the present invention is a hollow shell obtainable by disintegrating the template biomolecules of the coated particle as described above. The hollow shell may be an organic structure, an inorganic structure or a composite organic-inorganic structure depending on the method used to remove the core.

The coated particle may be used as a system for targeted delivery and/or controlled release of encapsulated crystallized and/or solubilized substances.

Targeting may be accomplished by selecting specific nanoparticles and/or polyelectrolytes for the construction of the multilayer shell which provide specific functional properties allowing targeting of the resulting capsule. Examples of functional nanoparticles are nanoparticles which provide magnetic properties to the resulting capsules. Further examples of nanoparticles having targeting function are biomolecules such as specific immunoglobulins, receptor ligands etc. Controlled release of the encapsulated crystallized and/or solubilized substances is obtainable by choosing pH swellable, thermally or environmentally responsive and/or biodegradable polyelectrolyte and/or nanoparticle constituents of the capsule wall.

The coated particles may be used to prevent degradation of the encapsulated material, e.g. in the body of animals and humans. It can also be used to control the ability of the encapsulated material to permeate cell walls or biomembranes. It further can be used to control the immune-reaction of an organism against the encapsulated material by the nature of the capsule material.

Further, the invention is illustrated by the following figures and examples:

FIG. 1 is a scheme showing an embodiment of the process used to encapsulate biomolecules by using biocrystals as templates for the deposition of polymer multilayers. (1), (2) Polyelectrolyte layers are deposited step-wise onto the biocrystal templates by making use of the surface charge reversal that occurs upon adsorption of each layer. Each polyelectrolyte is removed by repeated centrifugation/wash cycles before the next layer is deposited. (3) Solubilisation of the biomolecule inside the polymer capsule by exposure to solutions of pH>6 or acidic (approximately pH<4) solutions in a morphology change of the polymer capsule. (4)

Release of the biomolecule by rupturing the polymer capsule may e. g. be achieved by exposure to solutions of pH>11. (5) Exposure of the encapsulated biomolecule to an oxidising solution results in decomposition of the biomolecule which then is expelled from the interior through polymer walls, leaving behind hollow polymer capsules that originally encapsulated the biomolecule.

1. METHODS

1.1 Catalase Crystal Encapsulation

The catalase enzyme crystals (Sigma, C-100) were washed twice with a chilled (4° C.) solution of 1 M potassium acetate at pH 5 (buffer), with intermittent centrifugation steps (500 g, 4 min, 4° C.) to remove the supernatant, prior to polymer coating. The polymer layers were assembled onto the enzyme crystals by the alternate depostion of poly(sodium 4-styrenesulfonate) (PSS), $M_W$ 70,000, and poly(allylamine hydrochloride) (PAH), $M_W$ 8,000–11,000, both obtained from Aldrich. PSS was dialyzed against water and lyophilized before use. The first layer was deposited by adding a 0.5 ml aliquot of a 5 mg/ml aqueous PSS solution (containing 1 M potassium acetate, pH 5, 4° C.) to 0.2 ml of the crystal suspension, occasionally shaking the suspension, and allowing 25 min for adsorption. The excess polyelectrolyte was removed by 3 repeated centrifugation (500 g; 4 min, 4° C.)/chilled buffer wash/ redispersion cycles. The next layer, PAH, was deposited from a 5 mg/ml solution containing 1 M potassium acetate (pH 5 at 4° C.) using the same procedure and conditions. Subsequent alternating PSS and PAH layers were deposited in identical fashion until the desired number of polymer multilayers was achieved. Hollow polymer capsules were obtained by exposing the polymer multilayer-coated capsules to a deproteinizer solution (Medical Instruments). The deproteinizer destroys the protein.

1.2 Determination of Catalase Activity

The enzyme was released from the polymer capsules by exposure to ultrasound for 5 min at 20° C. in 1 M phosphate buffer at pH 7 (this caused rupturing of the polymer walls). The catalase activity was determined using a standard enzyme activity assay (Biochemica Information, 15–16 Boehringer Mannheim (1987); Tijsen, Practice and Theory of Enzyme Immunoassays, 8th Impression (1993), Elsevier, 202–203): that is, by measuring the decomposition of the substrate hydrogen peroxide ($H_2O_2$) at 240 nm. The concentration of the catalase was determined spectrophotometrically at 280 nm and 405 nm (soret band). The specific acitvity of the uncoated catalase was measured in the same way and used for comparison.

1.3 Electrophoretic Mobility and Microscopy Measurements

Electrophoretic mobilities of the uncoated and polymer-multilayer coated enzyme crystals were measured using a Malvern Zetasizer 4 as described elsewhere (Caruso et al., J. Phys. Chem. B 102, 2011–2116 (1998); Sukhorukov, G. B. et al., Polym. Adv. Technol. 9, 759–767 (1998); Donath et al., Angew. Chem. Int. Ed. 37, 2201–2205 (1998). The mobility u was converted into a ξ-potential using the Smoluchowski relation $\xi = u\eta/\epsilon$, where $\eta$ and $\epsilon$ are the viscosity and permittivity of the solution, respectively. Atomic force microscopy (AFM) images were obtained using a Digital Instruments Nanoscope IIIa AFM in tapping mode (TM) on samples deposited onto cleaned glass slides and air-dried. Samples for transmission electron microscopy (TEM) were prepared by deposition of aqueous solutions of the hollow polymer capsules upon a carbon-coated copper grid, allowing them to air dry for one minute, and then blotting off the extra solution.

1.4 Proteolysis Experiment 10 mg of protease (Streptomyces griseus; Sigma P6911; activity=5.2 U/mg solid) was dissolved in 500 μl of phosphate buffered saline (PBS, pH 7.0)(100 U/ml) and used as the stock solution. 200 μl samples of the polyelectrolyte-coated catalase and solubilized catalase where separately incubated in a water bath at 37° C. with either 30 μl of the stock protease solution of 30 μl of PBS (control experiment). The starting activity of the catalase for all samples was approximately 12000 U/ml catalase. The starting activities were normalized to 100%. The final protease activity in the sample was 13000 U/ml. Proteolysis of the catalase was determined by measuring the decrease in the catalase enzyme activity. The catalase activity measurements where carried out according to the previously described method (i.e. by spectrophotometric detection (240 nm) of the decomposition of hydrogen peroxide, see Tijsen, Practice and Theory of Enzyme Immunoassays, Elsevier, 8th Impression (1993), pp. 202–203.15). 5 μl samples were diluted and used for the activity measurements.

2. Results

The basic approach using enzyme crystals as templates for encapsulation by polymer multilayers is illustrated in FIG. 1. The method takes advantage of the fact that catalase is a crystalline suspension in water at pH 5–6 and therefore can be treated as a colloidal particle. The catalase crystals exhibit a positive surface charge (Zeta potential=+20 mV) in water at pH 5 (catalase isoelectric point=5.8), as determined by electrophoretic mobility measurements.

Figure 2:
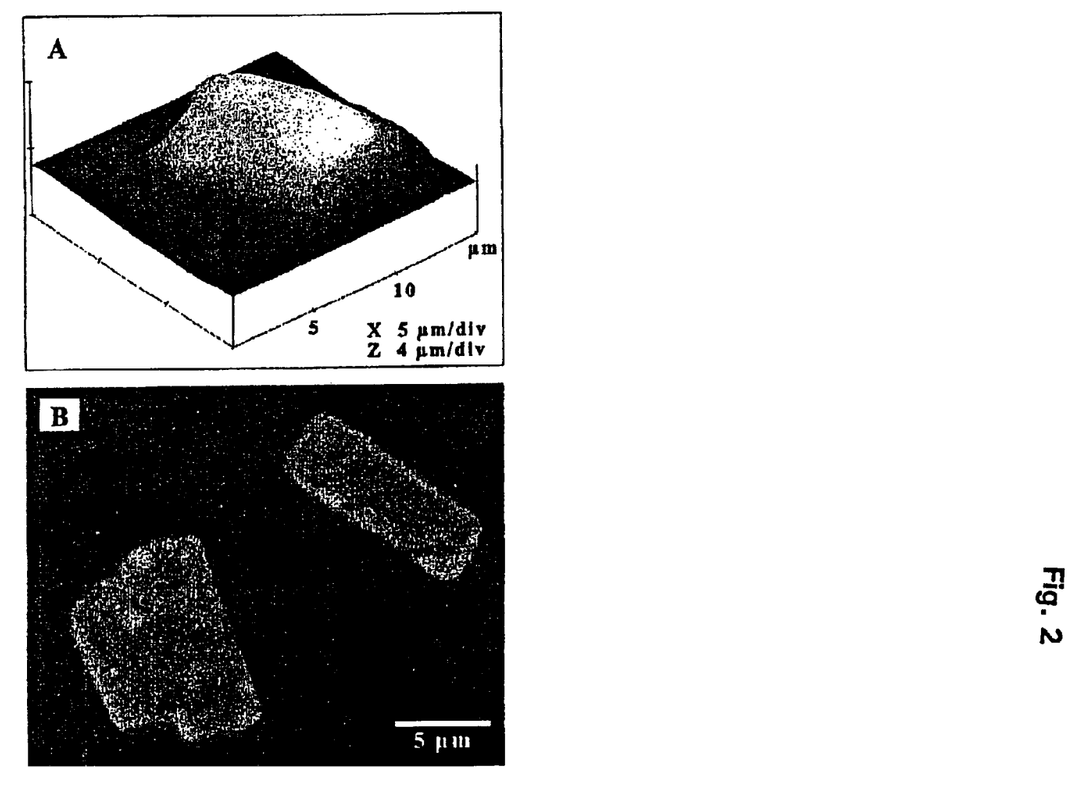
FIG. 2 shows images of uncoated and polymer-multilayer coated catalase crystals. a. AFM image of an uncoated crystal showing its essentially square shape and micrometer dimensions. b. Fluorescence optical micrographs of catalase crystals coated with eight [(PSS/FITC-PAH)$_4$] polyelectrolyte multilayers showing the applicability of the coating process to enzyme crystal templates. The polycation, PAH, deposited in alternation with the polyanion, PSS, is fluorescently labelled with fluorescein isothiocyanate (FITC). No noticeable change in crystal morphology is observed with the polymer multilayer coating.

A tapping mode atomic force microscopy (AFM) image of a catalase crystal, approximately 8×12 µm in size, is shown in FIG. 2(a). Next, the first polyelectrolyte layer, poly(styrenesulfonate) (PSS), which bears an opposite charge to the positively charged crystal surface, was added to the crystal suspension and allowed to self-assemble onto the crystal (FIG. 1). At this stage the enzyme crystal surface charge was reversed to a Zeta-potential of −30 mV, indicating the successful adsorption of PSS. Repeating alternating depositions of poly(allylaminehydrochloride) (PAH) and PSS produced crystals with alternating positive (+20 mV) and negative (−30 mV) surface potentials, respectively. These data clearly demonstrate recharging the surface.

In order to verify that the enzyme crystals are sucessfully coated with polymer multilayer shells, a fluorescently labelled polyelectrolyte (fluorescein isothiocyanate—(FITC)—PAH) was substituted for each alternate PAH deposition in the build-up process. The fluorescence, as seen under a fluorescence microscope, originates only from the surface of the polymer coated enzyme crystals (FIG. 2b). The fluorescence signal was found to increase systematically with an increasing number of fluorescent layers. No noticeable change in size or shape of the crystals were observed with the polymer multilayer shell coating. Further, the polymer-coated enzymes could be stored for at least 30 days at 4° C. without any noticeable change in morphology. These results show that enzyme crystals can be encapsulated within a polymer multilayer capsule via the step-wise and regular assembly of oppositely charged polymers, and that the crystal size and shape is retained upon their coating.

Figure 3:
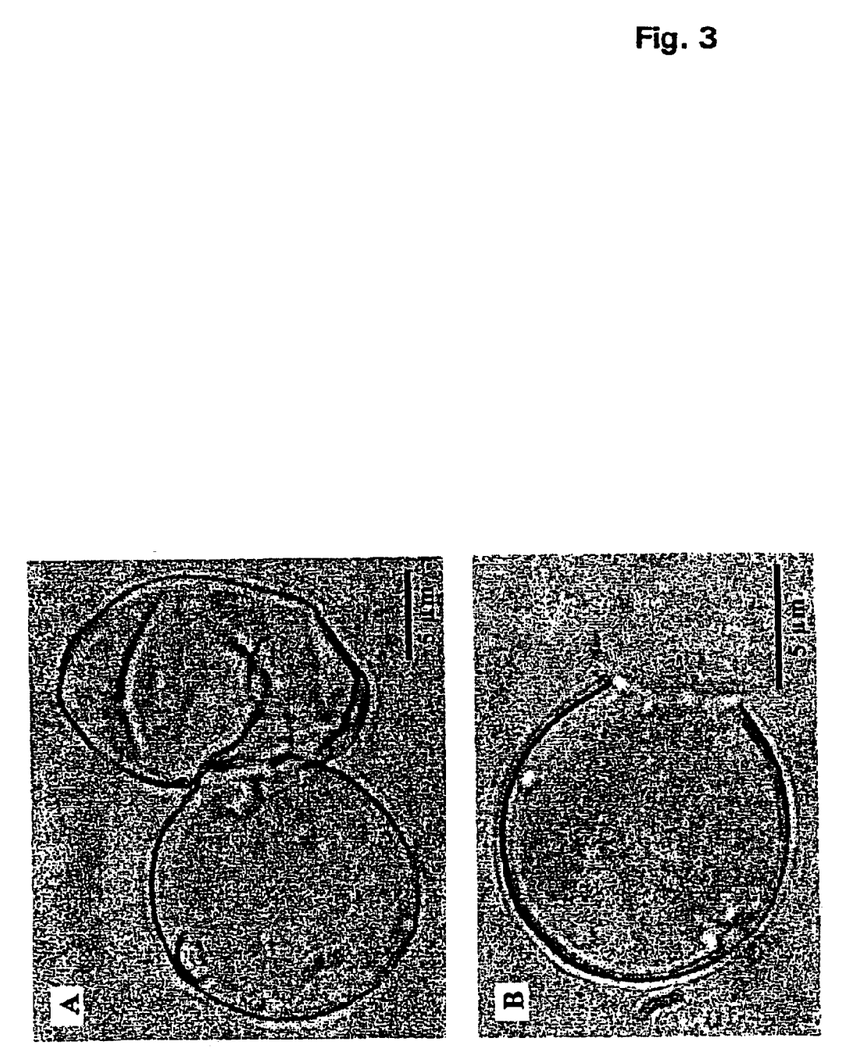
FIG. 3 shows representative optical micrographs of the polymer capsules encapsulating solubilised enzyme. a. A polymer capsule containing solubilized enzyme in its interior. The essentially spherical shape is assumed upon solubilisation of the enzyme as a result of exposure to solutions of pH>6. Solubilization also occurs upon exposure to solutions of pH<4. b. Rupturing of a polymer capsule causes the release of the entrapped, solubilized enzyme. Rupturing is achieved by subjecting the polymer capsules to alkaline solutions of pH>11.

Exposure of the polymer multilayer-encapsulated enzyme crystals to a solution of pH<4 and pH>6 resulted in the polymer capsule assuming a more spherical shape (FIG. 3a). Similar morphology changes were observed for other coated crystals, although perfectly spherical capsules were not always observed (as seen in FIG. 3a). The morphology change of the polymer capsules at pH<4 and pH>6 is attributed to the solubilization of the enzyme crystal, which occurs because the polymer multilayers are permeable to the mobile ions in the solution phase. The capsules did not rupture solely as a result of enzyme solubilization, indicating their high stability.

Evidence that the enzyme was encapsulated within the polymer capsules was obtained by deliberately rupturing the polymer shells. The polymer multilayer capsules were found to partially rupture upon exposure to alkaline solutions of pH>11. An optical micrograph image of shell rupture is displayed in FIG. 3b. Soon after shell wall rupture, solubilized enzyme is expelled from the interior of the capsule. The expulsion of the enzyme is caused by the osmotic pressure between the interior and exterior of the polymer capsules. Video microscopy verifies that the solubilized enzyme is expelled upon exposure to solutions of pH>11 as a result of capsule rupture. These data confirm that the solubilized enzyme is entrapped within the polymer capsules.

The catalase activity was measured after its solubilization and release from the polymer capsules. A recovered specific activity of 97% was obtained, compared with 100% for the uncoated catalase. This shows that the polymer coating of the catalase crystals proceeds without causing any significant loss of enzyme activity.

Figure 4:
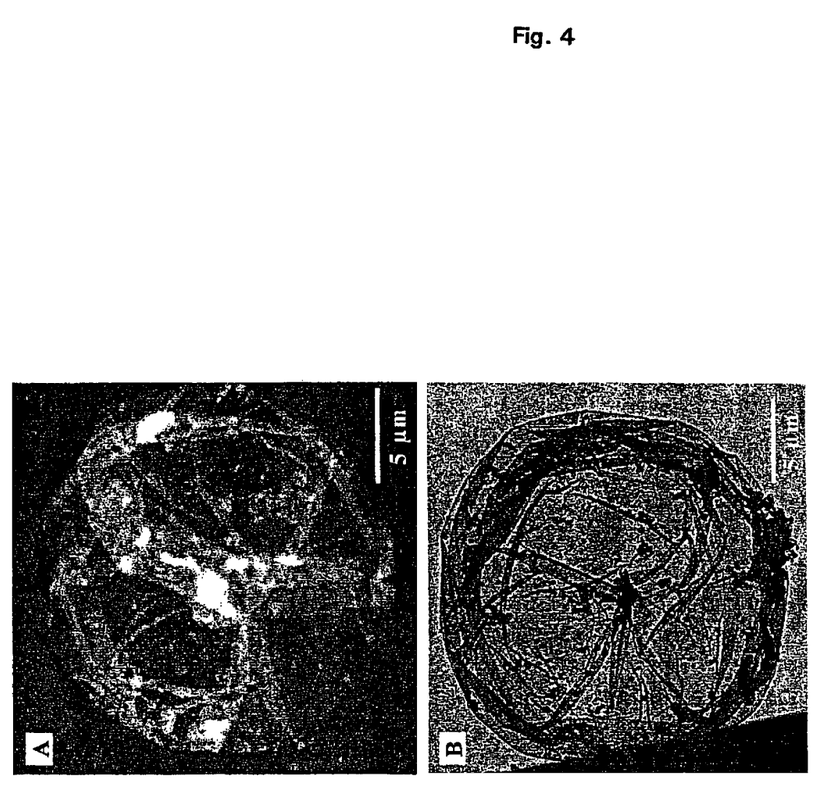
FIG. 4 shows micrographs of air-dried hollow polymer capsules obtained after decomposition of the encapsulated enzyme. a. AFM image of a polymer capsule comprising eight [(PSS/PAH)$_4$] polyelectrolyte layers. The polymer capsule spreads out on the glass surface on which it is dried and folds and creases in the shell can be seen. Some undecomposed enzyme can still be seen in the interior of the capsule. The z range (height) of the image is 650 nm. b. TEM image also shows folds and creases as well as the presence of a small amount of residual enzyme inside the capsule.

FIG. 4 shows representative AFM and TEM images of the air-dried polymer capsules, obtained after exposing the polymer-coated enzyme crystals to an oxidizing solution (deproteinizer). The enzymes are decomposed by the deproteinizing treatment, allowing the expulsion of their fragment constituents from the interior by permeating the polymer capsule walls. The polymer multilayer capsules remain intact, as can be seen in the images. The drying process (evaporation of the aqueous content by air-drying) induces a number of folds and creases in the polymer capsules. The shells are also flattened and some spreading is noticed; the diameters of the dried polymer capsules are approximately 20 µm. The texture of the shells is characteristic of the polyelectrolyte film, although some residual catalase can be seen in the capsules. From the AFM image for the polymer capsule, it can be deduced from the lowest height dimensions (35 nm), equivalent to twice the polymer capsule wall thickness, that the average thickness per polyelectrolyte layer is approximately 2 nm (the enzyme crystal templates were coated with eight layers). Cross-section TEM images and confocal microscopy show that hydrated polymer capsules maintain their spherical shape in solution, although spreading and creasing is observed on drying, as seen here after removal of the enzyme and subsequent drying.

Figure 5:
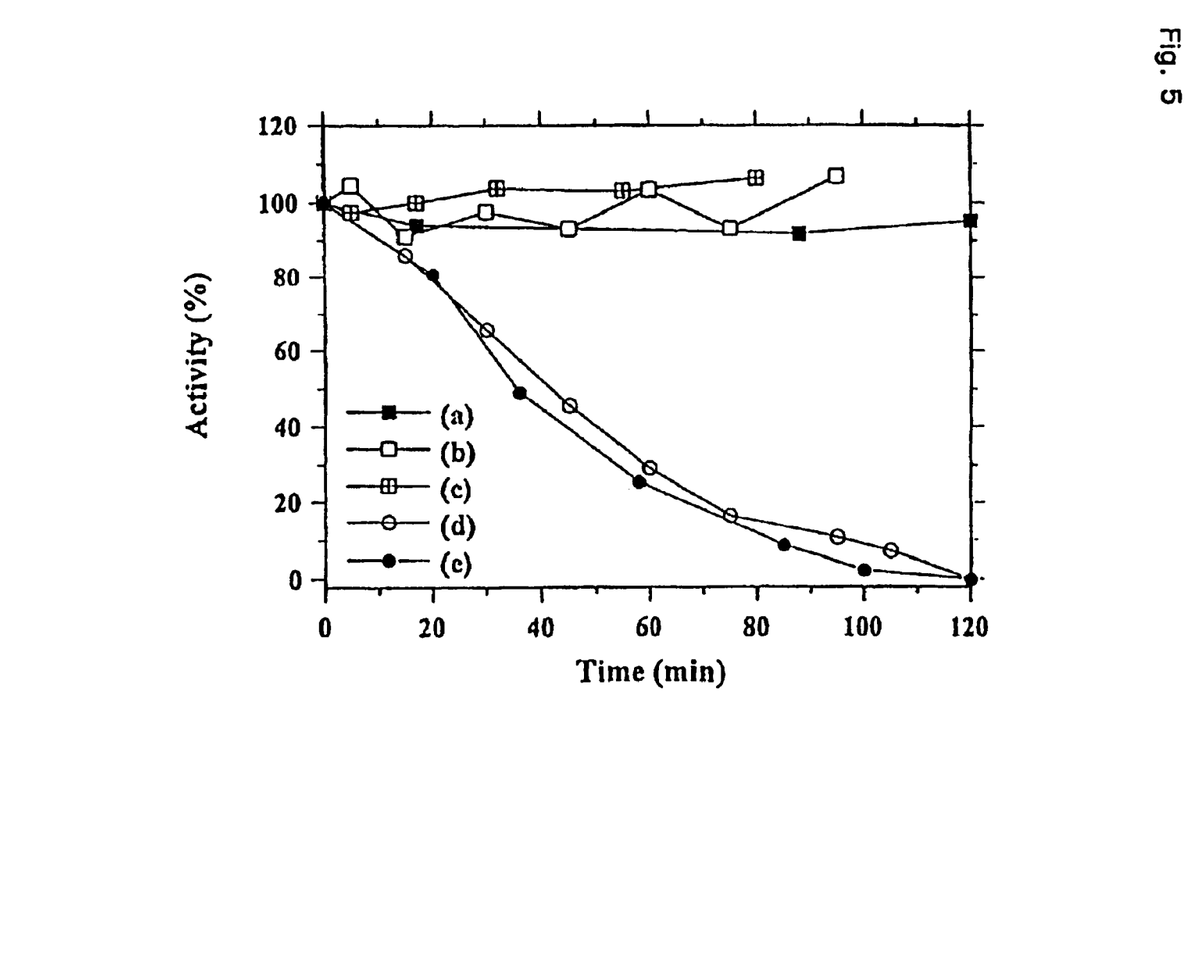
FIG. 5 shows the stability of (a, d, e) solution solubilized catalase and (b, c) polymer multilayer-encapsulated (solubilized) catalase with respect to proteolysis. (a) Solution solubilized catalase crystals, no protease incubation (control); (b) [(PSS/PAH)$_2$]-coated (4 layers) catalase, protease incubation; (c) [(PSS/PAH)$_4$]-coated (8 layers) catalase, protease incubation; (d) and (e) repeat experiments for solubilized catalase, protease incubation. Proteolysis of the catalase was determined by measuring the decrease in the catalase enzyme activity.

The results of the proteolysis experiments are shown in FIG. 5. Solubilized, uncoated catalase (curves d and e) was inactivated by protease to more then 90% during an incubation time of 100 min. In contrast, no measurable loss in enzyme activity was observed for the polymer-encapsulated (solubilized) catalase within 100 min under the same conditions (curves b and c). (The catalase was solubilized and retained within the polymer multilayer capsule at the experimental pH of 7). Further experiments showed that the activity of the encapsulated enzyme was fully retained after 24 hours exposure to protease. These results clearly demonstrate that a thin polymer coating of 4 layers (thickness of ca. 8 nm) is sufficient to prevent proteolysis of the polymer-encapsulated catalase.

What is claimed is:

1. A process for preparing coated crystals comprising the steps:
   a. providing a dispersion of bio-crystal template particles in a solvent and
   b. coating said particles with a multilayer comprising alternating layers of oppositely charged polyelectrolytes and/or nanoparticles.

2. The process of claim 1, wherein said bio-crystal particles are protein crystals, peptide crystals, nucleic acid crystals, lipid based crystals, carbohydrate crystals or crystals from low molecular weight materials.

3. The process of claim 2, wherein said protein crystals are selected from antibody crystals, enzyme crystals, virus capsid protein crystals, S-layer protein crystals, glycoprotein crystals, receptor protein crystals and cytostolic protein crystals.

4. The process of claim 1, wherein said bio-crystal template particles are selected from the group consisting of crystalline bio-material, crystalline organic material, crystalline inorganic material and mixtures thereof.

5. The process of claim 4, wherein the crystalline or organic material is selected from crystalline drugs, crystalline vitamins, crystalline nutrients, crystalline hormones, crystalline growth factors, crystalline pesticides and crystalline antibiotics.

6. The process of claim 1, wherein the bio-crystal template is a single crystal materials or an amorphous crystal material.

7. The process of claim 1, wherein said bio-crystal template particles have an average diameter of 500 µm or less.

8. The process of claim 7, wherein said bio-crystal template particles have an average diameter of 50 µm or less.

9. The process of claim 1, wherein said polyelectrolytes are linear models.

10. The process of claim 1, wherein said polyelectrolytes are selected from inorganic, organic and biological polyelectrolytes and mixtures thereof.

11. The process of claim 10, wherein the organic polyelectrolyte is a polymer selected from biodegradeable polymers, fluorescently labeled polymers, conducting polymers, liquid crystal polymers, photoconducting polymers, photochromic polymers, and copolymers and/or mixtures thereof.

12. The process of claim 10, wherein the biological polyelectrolyte is a polymer selected from polyamino acids, polycarbohydrates, polynucleotides and modified biopolymers.

13. The process of claim 10, wherein the inorganic polyelectrolyte is a polymer based on polysilanes, polysilanoles, polyphosphazanes, polysulfazenes, polysulfides and polyphosphates.

14. The process of claim 1, wherein said nanoparticles have an average diameter of from 1 to 100 nm.

15. The process of claim 1, wherein said nanoparticles are selected from inorganic, organic and biological particles and mixtures thereof.

16. The process of claim 15, wherein said nanoparticles are selected from particles which provide targeting properties.

17. The process of claim 16, wherein said nanoparticles are particles having magnetic properties.

18. The process of claim 16, wherein said nanoparticles are immunoglobins or receptor ligands.

19. The process of claim 15, wherein said nanoparticles are particles having magnetic properties.

20. The process of claim 15, wherein said nanoparticles are immunoglobins or receptor ligands.

21. The process of any one of claim 15 to 20, 17, or 18, wherein the inorganic nanoparticles are ceramic particles, magnetic particles, magneto-optical particles, nitridic ceramic particles, carbidic ceramic particles, metallic particles, and/or sulfur or selenium-containing particles.

22. The process of any one of claim 15 to 20, 17, or 18, wherein the organic or biological nanoparticles are macromolecules and/or targeting molecules.

23. The process of claim 1, wherein said solvent is selected from aqueous solvents, organic solvents and mixed aqueous/organic solvents.

24. The process of claim 1 further comprising the step:
  c. at least partially solubilizing the encapsulated bio-crystal.

25. The process of claim 24, wherein said solubilization is carried out by adjustment of solvent, pH, temperature and/or salt conditions.

26. The process of claim 1 further comprising the step:
  d. rupturing the polyelectrolyte/nanoparticle shell.

27. The process of claim 1 further comprising the step:
  e. at least partially disintegrating encapsulated bio-crystals.

28. Coated bio-crystal particle having a core which is a crystal template particle and a multilayer shell comprising alternating layers of oppositely charged polyelectrolytes and/or nanoparticles.

29. Coated bio-crystal particle having a core comprising an at least partially solubilized crystal template particle and a multilayer shell comprising alternating layers of oppositely charged nanoparticles and/or polyelectrolytes.

30. The particle of claim 28 or 29 having an average diameter of 50 µm or less.

31. A hollow shell obtainable by disintegrating the template particle of the coated particle of claim 30.

32. The use of the particle according to claim 30 as a system for targeted delivery and/or controlled release of crystallizable biomolecules.

33. A hollow shell obtainable by disintegrating the template particle of the coated particle of claim 28, or 29.

34. The use of the particle according to claim 28 or 29 as a system for targeted delivery and/or controlled release of crystallizable biomolecules.

* * * * *